United States Patent
Choi et al.

(10) Patent No.: US 9,220,779 B2
(45) Date of Patent: Dec. 29, 2015

(54) CARRIER FOR NEGATIVELY CHARGED DRUGS COMPRISING A CATIONIC LIPID AND A PREPARATION METHOD THEREOF

(75) Inventors: Sung-Won Choi, Daejeon (KR); Muhn-Ho La, Daejeon (KR); Ji-Yeon Son, Daejeon (KR); Min-Hyo Seo, Daejeon (KR)

(73) Assignee: SAMYANG BIOPHARMACEUTICALS CORPORATION, Seoul (KR)

(*) Notice: Subject to any disclaimer, the term of this patent is extended or adjusted under 35 U.S.C. 154(b) by 46 days.

(21) Appl. No.: 13/993,787

(22) PCT Filed: Dec. 30, 2011

(86) PCT No.: PCT/KR2011/010398
§ 371 (c)(1),
(2), (4) Date: Jun. 13, 2013

(87) PCT Pub. No.: WO2012/091523
PCT Pub. Date: Jul. 5, 2012

(65) Prior Publication Data
US 2013/0266641 A1 Oct. 10, 2013

(30) Foreign Application Priority Data

Dec. 30, 2010 (KR) .................. 10-2010-0138427

(51) Int. Cl.
| | |
|---|---|
| A61K 47/16 | (2006.01) |
| A61K 31/7105 | (2006.01) |
| A61K 47/48 | (2006.01) |
| A61K 9/107 | (2006.01) |
| A61K 9/127 | (2006.01) |
| C12N 15/88 | (2006.01) |
| A61K 47/18 | (2006.01) |
| A61K 47/28 | (2006.01) |

(52) U.S. Cl.
CPC .............. *A61K 47/16* (2013.01); *A61K 9/107* (2013.01); *A61K 9/1075* (2013.01); *A61K 9/1272* (2013.01); *A61K 31/7105* (2013.01); *A61K 47/48192* (2013.01); *A61K 47/48207* (2013.01); *C12N 15/88* (2013.01); *A61K 47/18* (2013.01); *A61K 47/28* (2013.01)

(58) Field of Classification Search
CPC . D06M 13/405; A61K 31/7105; A61K 47/18; A61K 47/48192; A61K 9/107
USPC .............................. 424/450; 514/44 A; 554/51
See application file for complete search history.

(56) References Cited

U.S. PATENT DOCUMENTS

| | | | |
|---|---|---|---|
| 3,658,718 A | 4/1972 | Clumpner | |
| 4,551,505 A | 11/1985 | Sauerbier | |
| 5,744,335 A * | 4/1998 | Wolff et al. | 435/458 |
| 2009/0090128 A1 | 4/2009 | Kaneko | |
| 2010/0275382 A1 | 11/2010 | Calvert | |
| 2011/0252825 A1 | 10/2011 | Kaneko | |
| 2011/0268772 A1* | 11/2011 | Kim et al. | 424/400 |

FOREIGN PATENT DOCUMENTS

| | | |
|---|---|---|
| AU | 2008315798 | 4/2009 |
| CN | 101341235 | 1/2009 |
| CN | 101835883 | 5/2014 |
| EP | 1975221 | 10/2008 |
| JP | 61-500729 | 4/1986 |
| JP | 08-183979 | 7/1996 |
| JP | 2007-056427 | 3/2007 |
| JP | 2009-243022 | 10/2009 |
| KR | 10-2010-0076905 | 7/2010 |
| KR | 10-2010-0087123 | 8/2010 |
| WO | 2008-042973 | 4/2008 |

OTHER PUBLICATIONS

Li et al.; Title: SUrface-modifeid LPD nanoparticla for tumor targeting; Ann. N. Y. Acad. Sci. 1082:1-8, 2006.*
Schiffelers et al; title: Transporting silence: design of carriers for siRNA to angiogenic endothelium; (J Control Release. Dec. 5, 2005; 109(1-3):5-14. Epub Jun. 24, 2005.*
Surfactatn definition, downloaded from https://www.wordnik.com/words/surfactanton Feb. 6, 2015.*
International Searching Authority, International Search Report of PCT/KR2011/010398 (Sep. 27, 2012).
Vijay P et al., "DNA delivery in vitro via surface release from multilayer assemblies with poly(glycoamidoamine)s," Acta Biomaterialia vol. 5, p. 925-933, Department of Chemistry at Virginia Tech, Blacksburg, VA, USA (Jan. 13, 2009).
Jong Woan Kim, Yong Ryul Kim and U Youn Lee, "Synthesis and Antibacterial Activity of Polyacrylic Acid (PAA)-Sulfacetamide", Kor. J. Env. Hlth. Soc., vol. 27, No. 1, p. 106-111(Mar. 2001).
Nilesh P. Ingle, Brett Malone and Theresa M. Reineke, "Poly(glycoamidoamins)s: a broad class of carbohydrate-containing polycations for nucleic acid delivery" Trends in Biotechnology, vol. 29, No. 9, p. 443-453 (Sep. 2011).
Vijay P. Taori, Yemin Liu, Theresa M. Reineke, "DNA delivery in vitro via surface release from multilayer assemblies with poly(glycoamidoamine)s", Acta Biomaterialia 5 (2009) p. 925-933 (Jan. 2009).
Japan Patent Office, The Office Action dated Mar. 31, 2015, Japanese Patent Application No. 2013547365.

* cited by examiner

*Primary Examiner* — Johann R Richter
*Assistant Examiner* — Yanzhi Zhang
(74) *Attorney, Agent, or Firm* — LEX IP Meister, PLLC

(57) ABSTRACT

Disclosed are a carrier for delivering a negatively charged drug, comprising a cationic lipid represented by formula 1, and a preparation method thereof. Also disclosed is a pharmaceutical composition comprising a negatively charged drug and a cationic lipid represented by formula 1, wherein the negatively charged drug forms a complex with the cationic lipid. The composition can increase the in vivo stability of the negatively charged drug after local or systemic administration and allows the intracellular delivery of the negatively charged drug. Thus, the composition will be useful for improving the therapeutic effect of the negatively charged drug.

9 Claims, 8 Drawing Sheets

SEQUENCE LISTING

<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: sense sequence of GFP siRNA with dTdT attached to the 3' end

<400> SEQUENCE: 1
gcaagcugac ccugaaguu                                                19

<210> SEQ ID NO 2
<211> LENGTH: 19
<212> TYPE: RNA
<213> ORGANISM: Artificial Sequence -continued

```
<220> FEATURE:
<223> OTHER INFORMATION: antisense sequence of GFP siRNA with dTdT
      attached to the 3' end

<400> SEQUENCE: 2
aacuucaggg ucagcuugc                                              19
```

CARRIER FOR NEGATIVELY CHARGED DRUGS COMPRISING A CATIONIC LIPID AND A PREPARATION METHOD THEREOF

TECHNICAL FIELD

The present invention relates, in general, to a carrier for delivering a negatively charged drug, comprising a cationic lipid, and a preparation method thereof, and, more particularly, to a composition for delivering a negatively charged drug, wherein the negatively charged drug forms a complex with a cationic lipid of formula 1 of the present invention, and a preparation method thereof.

BACKGROUND ART

Safe and efficient drug delivery techniques have been studied for a long time, and various delivery systems and techniques have been developed, in the field of treatment using negatively charged drugs, particularly nucleic acid substances. Particularly, delivery techniques employing viral delivery systems based on an adenovirus or a retrovirus, and non-viral delivery systems based on cationic lipids or cationic polymers have been developed.

However, it is known that the techniques employing the viral delivery systems are exposed to risks, including non-specific immune responses, and that their commercial use presents a number of problems due to the production processes being complex. For this reason, a recent research trend is to overcome the shortcomings of viral delivery systems is to use non-viral delivery systems based on cationic lipids or cationic polymers. Such non-viral delivery systems are less efficient than viral delivery systems, but have the advantages of being accompanied by fewer side effects in vivo and having a low production cost.

Among non-viral delivery system formulations, polycationic polymers that electrostatically bind to nucleic acid substances to form nucleic acid-polymer complexes have been used, but there are a number of problems that occur when actually used because of the cytotoxicity of the polycationic charges.

Also, cationic lipids can be used, but are difficult to use in vivo, because the stability of nucleic acid-lipid complexes in blood is low. Moreover, it has been attempted to use ionic liposomes, including cationic lipids, neutral lipids and fusogenic lipids, as systemic delivery systems, but the cationic lipids are complex to synthesize and are still cytotoxic, and the efficiency of intracellular nucleic acid delivery thereof is low.

In addition, techniques in which complexes of cationic lipids with siRNA are formed and the complexes are entrapped in the micelles of amphiphilic block copolymers are known. However, the synthesis and purification process of the cationic cholesterol lipids that are used in these techniques are complex.

Meanwhile, many diseases are caused by an increased expression of disease-related genes which happens because of various factors or by abnormal activity which is caused by mutation. siRNA (small interfering RNA) inhibits the expression of a specific gene in a sequence-specific manner at the post-transcriptional stage, and receives a great deal of attention as a gene therapeutic agent. Particularly, due to its high activity and precise genetic selectivity, siRNA is expected as a nucleic acid therapeutic agent that can substitute for existing antisense nucleotides or ribozymes. siRNA is a short double-stranded RNA molecule composed of 15-30 nucleotides and cleaves the mRNA of a gene having a nucleotide sequence complementary thereto to inhibit the expression of the gene.

However, siRNA is rapidly degraded by nucleases in the blood and does not easily pass through the cell membrane because it is negatively charged. For this reason, in order to use siRNA as a therapeutic agent, it is required to use a composition which allows siRNA to be efficiently delivered into a targeted cell or an organ while siRNA circulates in the blood over a long period.

DISCLOSURE

Technical Problem

Accordingly, one embodiment of the present invention provides a carrier for delivering a negatively charged drug, comprising a cationic lipid represented by formula 1.

Another embodiment of the present invention provides a method of preparing the carrier comprising the step of reacting an oligoalkyleneamine with acyl halides of fatty acid; to prepare a cationic lipid of formula 1.

Still another embodiment of the present invention provides a pharmaceutical composition comprising a negatively charged drug and a cationic lipid represented by formula 1, wherein the negatively charged drug forms a complex with the cationic lipid.

Still another embodiment of the present invention provides a micelle composition comprising a negatively charged drug, a cationic lipid of formula 1 and an amphiphilic block copolymer, wherein the negatively charged drug forms a complex with the cationic lipid, and the complex is entrapped in the micelle structure of the amphiphilic block copolymer, as well as a preparation method thereof.

Still another embodiment of the present invention provides a liposome composition comprising a negatively charged drug, a cationic lipid of formula 1 and a cell-fusogenic phospholipid, wherein the negatively charged drug forms a complex with the cationic lipid, and the complex is bound to a liposome consisting of the cell-fusogenic phospholipid.

Yet another embodiment of the present invention provides a micelle composition comprising a negatively charged drug, a cationic lipid of formula 1 and a surfactant, wherein the negatively charged drug forms a complex with the cationic lipid, and the complex is entrapped in the micelle structure of the surfactant.

Still another object of the present invention provides an emulsion composition comprising a negatively charged drug, a cationic lipid of formula 1 and a surfactant, wherein the negatively charged drug forms a complex with the cationic lipid, and the complex is entrapped in an emulsion.

Technical Solution

The present invention provides a carrier for delivering a negatively charged drug, comprising a cationic lipid represented by formula 1:

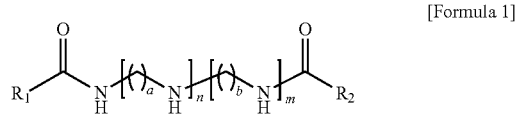

[Formula 1]

wherein n and m are independently 0 to 12, with the proviso that $2 \leq n+m \leq 12$, a and b are independently 1 to 6, and R1 and R2 are independently saturated or unsaturated hydrocarbon groups having 11 to 25 carbon atoms.

The cationic lipid represented by formula 1 consists of a positively charged oligoalkyleneamine and a hydrophobic saturated or unsaturated fatty acid having 12 to 26 carbon atoms, which are linked by an amide bond. In the present invention, the cationic lipid may be bound to a negatively charged drug by electrostatic interaction to form a complex, which increases the in vivo stability of the negatively charged drug and allows the negatively charged drug to be delivered into cells.

In one preferred embodiment of the present invention, n and m are independently 1 to 9, with the proviso that $2 \leq n+m \leq 10$. More preferably, n and m are independently 1 to 3, with a proviso that $3 \leq n+m \leq 6$. The oligoalkyleneamine preferably has n and m values within the above-specified ranges in order to maintain the density of the fatty acid at a high level and to minimize the cytotoxicity of the cation.

In formula 1, a and b are each preferably 2 to 4, and more preferably 2. If a and b are smaller than 1, the distance between the amines will be so short that the electrostatic interaction between the cationic lipid and the negatively charged drug will decrease. On the other hand, if a and b are greater than 6, the distance between the amines will be too long and the density of the cations will decrease, so that the electrostatic interaction between the cationic lipid and the negatively charged drug will decrease, and thus a stable complex therebetween cannot be formed.

Specifically, the oligoalkyleneamine that is used in the present invention may be oligoethyleneamine, and more specifically one or more selected from the group consisting of diethylenetriamine, triethylenetetramine, tetraethylenepentamine, pentaethylenehexamine, hexaethyleneheptamine, heptaethyleneoctamine, octaethylenenonamine, nonaethylenedecamine, decaethyleneundecamine, undecaethylenedodecamine, dodecaethylenetridecamine and tridecaethylenetetradecamine. Preferably, it is triethylenetetramine, tetraethylenepentamine, pentaethylenehexamine or hexaethyleneheptamine.

R1 and R2 may preferably be each saturated or unsaturated hydrocarbon groups having 11 to 25 carbon atoms, and more preferably unsaturated hydrocarbon groups having 13 to 21 carbon atoms. If the number of carbon atoms in each of R1 and R2 is smaller than 11, the hydrophobic interaction between the hydrocarbon chains can decrease, and thus a stable formulation cannot be formed. On the other hand, if the number of carbon atoms is larger than 25, the hydrophobic interaction between the hydrocarbons will increase, and thus the formulation will be excessively stable, whereby the in vivo dissociation of the drug will decrease, leading to a decrease in the efficacy of the drug. In addition, the curvature of the hydrocarbon chains will increase due to an increase in cis double bonds, and thus the resulting formulation will have low density and thus low stability.

The saturated hydrocarbon groups may specifically include lauryl, myristyl, palmityl, stearyl, arachidyl, behenyl, lignoceryl, cerotyl groups, etc. The unsaturated hydrocarbon groups preferably have a cis bond and may specifically include myristoleyl, palmitoleyl, sapienyl, oleyl, linoleyl, arachidonyl, eicosapentaenyl, erucyl, docosahexaenyl groups, etc.

The present invention also provides a method for preparing the drug carrier, comprising the step of reacting an oligoalkyleneamine represented by the following formula 2 with an acyl halide of fatty acid represented by the following formula 3 and an acyl halide of fatty acid represented by the following formula 4, to prepare a cationic lipid of formula 1:

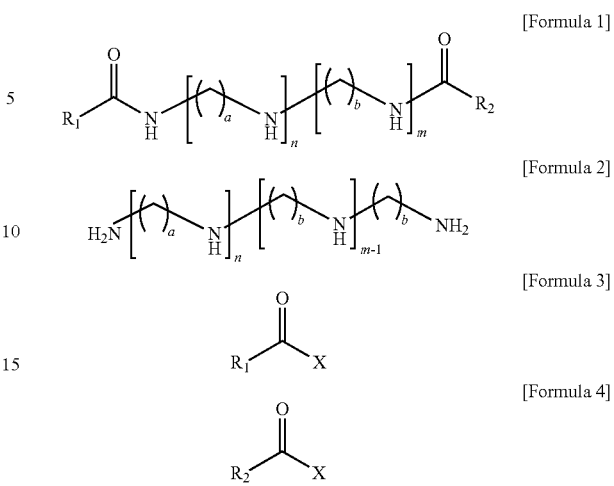

wherein n and m are independently 0 to 12, with a proviso that $2 \leq n+m \leq 12$, a and b are independently 1 to 6, and R1 and R2 are independently saturated or unsaturated hydrocarbon groups having 11 to 25 carbon atoms, and X is a halogen In one embodiment of the present invention, the cationic lipid of formula 1 may be prepared by reacting an oligoalkyleneamine with acyl halides of fatty acid corresponding to the product of formula 1. Specifically, it may be prepared through the reaction shown in reaction scheme 1:

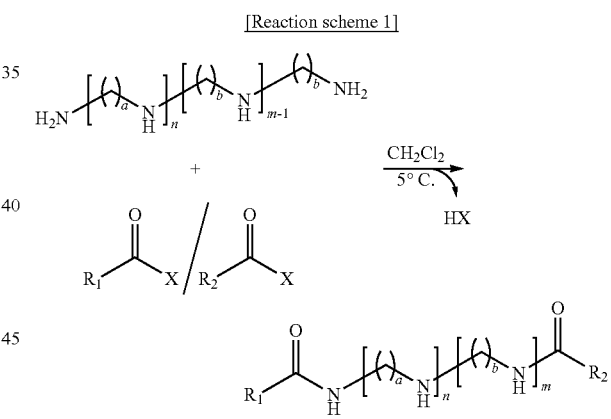

wherein R1 and R2, a, b, n and m are as defined above for formula 1, and X is a halogen, including fluorine, chlorine, bromine or iodine.

Specifically, the cationic lipid of the present invention is an amphiphilic compound consisting of a hydrophilic oligoalkyleneamine and a hydrophobic fatty acid, which are linked by an amide bond, in which the amide bond can be formed between the primary amine group (—NH$_2$) at the end of the oligoalkyleneamine and the fatty acid.

In the above preparation method, the acyl halide of fatty acid is an acyl halide derived from a fatty acid having 12 to 26 carbon atoms. Preferred examples of acyl halides of saturated fatty acid that may be used as acyl halides of fatty acid in the present invention include lauroyl chloride, myristoyl chloride, palmitoyl chloride, stearoyl chloride, arachidoyl chloride, behenoyl chloride, lignoceroyl chloride, cerotoyl chloride, etc., with more preferred being palmitoyl chloride, stearoyl chloride, arachidoyl chloride and behenoyl chloride.

Also, unsaturated fatty acid acyl chloride that may be used as the fatty acid acyl halide in the present invention preferably has a cis double bond, and preferred examples thereof include myristoleoyl chloride, palmitoleoyl chloride, sapienoyl chloride, oleoyl chloride, linoleoyl chloride, arachidonoyl chloride, eicosapentaenoyl chloride, erucoyl chloride, docosahexaenoyl chloride, etc., with more preferred being myristoleoyl chloride, palmitoleoyl chloride, sapienoyl chloride, oleoyl chloride, linoleoyl chloride, arachidonoyl chloride, and eicosapentaenoyl chloride.

One embodiment of the present invention provides a pharmaceutical composition comprising a negatively charged drug and a cationic lipid represented by formula 1, wherein the negatively charged drug forms a complex with the cationic lipid. In the present invention, the negatively charged drug and the cationic lipid represented by formula 1 electrostatically interact with each other to form a complex which acts to increase the in vivo stability of the negatively charged drug and mediates the intracellular delivery of the negatively charged drug.

The negatively charged drug according to one embodiment of the present invention is meant to include any pharmacologically active substances that bear negative charges in the molecule in an aqueous solution. In one embodiment, the anionic nature can be imparted from one or more functional groups selected from the group consisting of carboxyl, phosphate and sulfate groups. In one embodiment of the present invention, the negatively charged drug may be a polyanionic drug or a nucleic acid. Examples of the polyanionic drug may include heparin, calcitonin, etc.

The nucleic acid may be a nucleic acid drug, such as deoxyribonucleic acid, ribonucleic acid, or a polynucleotide derivative wherein the backbone, sugar or base is chemically modified or the end of the nucleic acid is modified. More preferably, it may be one or more nucleic acid selected from the group consisting of RNA, DNA, siRNA (small interfering RNA), an aptamer, antisense oligodeoxynucleotide (ODN), antisense RNA, ribozyme and DNAzyme. Also, in order to increase the stability of the nucleic acid in blood or weaken the immune response, the backbone, sugar or base of the nucleic acid may be chemically modified or the end of the nucleic acid may be modified. Specifically, a portion of the phosphodiester bond of the nucleic acid may be substituted by a phosphorothioate or boranophosphate bond, or the nucleic acid may include at least one nucleotide wherein various functional groups such as a methyl group, a methoxyethyl group or fluorine are introduced in the 2'-OH position of some riboses.

In another embodiment, one or more ends of the nucleic acid may be modified with one or more selected from the group consisting of cholesterol, tocopherol, and a fatty acid having 10-24 carbon atoms. For example, siRNA may be modified at the 5' end or at the 3' end or at both ends of the sense and/or antisense strand, and preferably at the end of the sense strand.

The above cholesterol, tocopherol and fatty acid may include their analogues, derivatives and metabolites.

In the present invention, the negatively charged drug is preferably contained in an amount of 0.001 to 10 wt %, particularly 0.01 to 5 wt %, based on the total weight of the composition. If the content of the negatively charged drug is less than 0.001 wt %, the amount of the delivery system will excessively increase compared to the amount of the drug, and this can cause side effects; likewise, if the content is more than 10 wt %, the delivery system may be less stable or the size thereof may excessively increase, and thus the rate of loss thereof during filter sterilization can increase.

The cationic lipid and the negatively charged drug are bound to each other by electrostatic interaction to form a complex. In one embodiment, the ratio of charge of the cationic lipid (N) to the negatively charged drug (P), (N/P), is 0.1 to 128, preferably 0.5 to 32, and more preferably 1-16. If the ratio (N/P) is less than 0.1, it will be difficult to form a complex containing a sufficient amount of the negatively charged drug. For this reason, the ratio (N/P) should be 0.1 or more such that a complex containing a sufficient amount of the negatively charged drug can be formed. On the other hand, if the ratio (N/P) is more than 128, the resulting complex can be cytotoxic.

In an embodiment of the present invention, the drug delivery composition comprising the cationic lipid serves to mediate the intracellular delivery of the nucleic acid and increase the in vivo stability of the negatively charged drug.

The pharmaceutical composition of the present invention may be a formulation selected from the group consisting of liposome, micelle, emulsion and nanoparticle formulations. Specifically, it may be a formulation wherein the negatively charged drug and the cationic lipid form a complex with each other and the complex is entrapped in a micelle, a liposome, an emulsion or a nanoparticle or bound to the surface.

In the above formulation, the negatively charged drug of the present invention is contained in an amount of 0.001 to 10 wt %, and preferably 0.01 to 5 wt %, based on the total weight of the composition. If the content of the negatively charged drug is less than 0.001 wt %, the amount used of the delivery system will excessively increase compared to the amount of the drug, and this can cause side effects; likewise, if the content is more than 10 wt %, the delivery system may be less stable or the size thereof can excessively increase, and thus the rate of loss thereof during filter sterilization can increase.

In the above formulation, the cationic lipid may be contained in an amount of 0.01 to 50 wt %, and preferably 0.1 to 10 wt %, based on the total weight of the composition. If the content of the cationic lipid is less than 0.01%, it will not be enough to form a complex with the negatively charged drug. And if the content is more than 50 wt %, the size of the delivery system will excessively increase, and thus the in vivo stability thereof can decrease and the rate of loss thereof during filter sterilization can increase. Moreover, cytotoxicity can be induced by excess cations.

In another embodiment of the present invention, the micelle formulation comprises an anionic drug, a cationic lipid and an amphiphilic block copolymer. Specifically, the present invention provides a liposome composition comprising a negatively charged drug, a cationic lipid of formula 1 and a cell-fusogenic phospholipid, wherein the negatively charged drug forms a complex with the cationic lipid, and the complex is bound to a liposome consisting of the cell-fusogenic phospholipid, as well as a preparation method thereof.

The amphiphilic block copolymer may be an A-B-type block copolymer comprising a hydrophilic A-block and a hydrophobic B-block. In an aqueous solution, the amphiphilic A-B-type block copolymer forms a core-shell type polymeric micelle, wherein the hydrophobic B-block forms a core having a negatively charged drug/cationic lipid complex entrapped therein and the hydrophilic A-block forms a shell exposed to the outside of the core.

In one embodiment, the hydrophilic A-block may be at least one selected from the group consisting of polyalkyleneglycol, polyvinyl alcohol, polyvinyl pyrrolidone, polyacrylamide, and derivatives thereof. More preferably, the hydrophilic A-block may be at least one selected from the group consisting of monomethoxy polyethylene glycol, monoacetoxy polyethylene glycol, polyethylene glycol, a copolymer of polyethylene and propylene glycol, and polyvinyl pyrrolidone. In another embodiment, the number-average molecular weight of the hydrophilic A-block may be 200 to 50,000 Daltons, preferably 1,000 to 20,000 Daltons, and more preferably 1,000 to 5,000 Daltons.

If necessary, a functional group or ligand that can reach a specific tissue or cell, or a functional group capable of promoting intracellular delivery may be chemically conjugated to the end of the hydrophilic A-block so as to control the in vivo distribution of the polymeric micelle delivery system or increase the efficiency of intracellular delivery thereof. The functional group or ligand may be at least one selected from the group consisting of monosaccharides, polysaccharides, vitamins, peptides, proteins, and antibodies to cell surface receptors. More preferably, it may be at least one selected from the group consisting of anisamide, vitamin B9 (folic acid), vitamin B12, vitamin A, galactose, lactose, mannose, hyaluronic acid, RGD peptide, NGR peptide, transferrin, an antibody to transferring receptor, and the like.

The hydrophobic B-block is a polymer having excellent biocompatibility and biodegradability. In one embodiment, it may be at least one selected from the group consisting of polyester, polyanhydride, polyamino acid, polyorthoester, and polyphosphazine. More preferably, the hydrophobic B-block may be at least one selected from the group consisting of polylactide, polyglycolide, polycaprolactone, polydioxane-2-one, a copolymer of polylactide and glycolide, a copolymer of polylactide and polydioxane-2-one, a copolymer of polylactide and polycaprolactone, and a copolymer of polyglycolide and polycaprolactone. In one embodiment, the number-average molecular weight of the hydrophobic B-block may be 50 to 50,000 Daltons, preferably 200 to 20,000 Daltons, and more preferably 1,000 to 5,000 Daltons. Also, to increase hydrophobicity of the hydrophobic block to improve the stability of the micelle, tocopherol, cholesterol, or a fatty acid having 10-26 carbon atoms may be chemically bound to the hydroxyl group at the end of the hydrophobic block.

The amphiphilic block copolymer comprising the hydrophilic block (A) and the hydrophobic block (B) may be contained in an amount of 40-99.98 wt %, preferably 85-99.8 wt %, and more preferably 90-99.8 wt %, based on the total dry weight of the composition. If the content of the amphiphilic block copolymer is less than 40 wt %, the size of the micelle can become so large that the stability of the micelle can decrease and the loss thereof during filter sterilization can increase; likewise, if the content is more than 99.98 wt %, the content of negatively charged drug that can be incorporated can become too small.

In another embodiment, with respect to the ratio between the contents of the hydrophilic block (A) and the hydrophobic block (B), the amphiphilic block copolymer may comprise 40 to 70 wt % of the hydrophilic block (A), and preferably 50 to 60 wt % of the hydrophilic block (A), based on the weight of the copolymer. If the content of the hydrophilic block (A) in the copolymer is less than 40 wt %, the solubility of the copolymer in water will be low, making it difficult to form a micelle from the copolymer. For this reason, the content of the hydrophilic block (A) in the copolymer is preferably 40 wt % or more in order for the copolymer to have water solubility sufficient for forming a micelle. On the other hand, if the content is more than 70 wt %, the hydrophilicity of the copolymer will be too high and so the stability of the polymeric micelle will be low, and thus it will be difficult to solubilize a complex of the negatively charged drug and the cationic lipid. For this reason, the content of the hydrophilic block (A) in the copolymer is preferably 70 wt % or less in view of the stability of the micelle.

In one embodiment, a complex of the negatively charged drug and the cationic lipid in the micelle structure is entrapped in the micelle structure of the amphiphilic block copolymer in an aqueous solution, wherein the ratio of the weight of the negatively charged drug/cationic lipid complex (a) to the weight of the amphiphilic block copolymer (b), [a/b×100; (the weight of the negatively charged drug+the weight of the cationic lipid)/the weight of the amphiphilic block copolymer×100], may be 0.001-100 wt %, preferably 0.01-50 wt %, and more preferably 0.1-10%. If the weight ratio is less than 0.001 wt %, the content of the complex of the negatively charged drug and the cationic lipid can decrease, and thus it can be difficult to satisfy the effective content of the negatively charged drug, and if it is more than 100 wt %, a micelle structure of the appropriate size cannot be formed after taking into consideration the molecular weight of the amphiphilic block copolymer and the amount of the negatively charged drug/cationic lipid complex.

Meanwhile, a method for preparing the micelle composition according to the present invention comprises the steps of:

(a) dissolving a negatively charged drug and a cationic lipid of formula 1 in a water-miscible organic solvent or a mixed solvent of an aqueous solution and an organic solvent and subjecting the solution to phase separation;

(b) separating an organic solvent layer formed in step (a);

(c) adding an amphiphilic block copolymer to the organic solvent layer resulting from step (b) and removing the organic solvent; and (d) adding an aqueous solution to the mixture from which the organic solvent had been removed, to form a micelle.

In step (a), the negatively charged drug and the cationic lipid are mixed in a water-miscible organic solvent or a mixed solvent of an aqueous solution and an organic solvent to form a complex. Specifically, the water-miscible organic solvent may be at least one selected from the group consisting of acetone, ethanol, methanol, and acetic acid, and the organic solvent in the mixed solvent may be at least one selected from the group consisting of ethyl acetate, acetonitrile, methylene chloride, chloroform, and dioxane. The aqueous solution may be distilled water, water for injection, or a buffer solution. The amount of the complex of the negatively charged drug and the cationic lipid dissolved in the solvent may be 0.1-100 wt %, preferably 0.1-10 wt %, and more preferably 0.1-1 wt %, based on the amount of solvent used. If the amount of the complex is 100 wt % or more, yield can rapidly decrease when the complex of the negatively charged drug and the cationic lipid is extracted with an organic solvent in step (b).

In step (b), the complex of the negatively charged drug and the cationic lipid is recovered by phase separation. An aqueous solvent and an organic solvent may be added to the solvent of step (a) to induce phase separation. Also, to shorten the phase separation time, a centrifugation process may be performed.

In step (c), an amphiphilic block copolymer is added to and mixed with the extracted organic solvent layer, and then the organic solvent is removed by evaporation.

In step (d), the mixture remaining after evaporation of the organic solvent is dissolved in an aqueous solution, whereby the complex of the negatively charged drug and the cationic lipid is entrapped in the micelle structure of the amphiphilic block copolymer. The aqueous solution may be distilled water, water for injection, or buffer solution, and the amount of aqueous solution used may be such that the concentration of the amphiphilic block copolymer may be about 10-300 mg/mL. If the concentration of the amphiphilic block copolymer is less than 10 mg/mL, the volume of the aqueous solution will increase, thus making it difficult to handle the aqueous solution during the preparation process; likewise, if it is more than 300 mg/mL, the viscosity of the aqueous solution will increase, thus making it difficult to prepare a micelle in a smooth manner.

In yet another embodiment of the present invention, a method of preparing a pharmaceutical composition comprising a negatively charged drug, a cationic lipid of formula 1 and an amphiphilic block copolymer comprises the steps of:

(a') dissolving the negatively charged drug, the cationic lipid and the amphiphilic block copolymer in a water-miscible organic solvent or a mixed solvent of an aqueous solution and an organic solvent;

(b') removing an organic solvent layer formed in step (a'); and (c') adding an aqueous solution to the mixture of (b') from which the organic solvent had been removed, to form a micelle.

In step (a'), the negatively charged drug, the cationic lipid, and the amphiphilic block copolymer are mixed in a water-miscible organic solvent or a mixed solvent of an aqueous solution and an organic solvent to form a complex. Specifically, the water-miscible organic solvent may be at least one selected from the group consisting of acetone, ethanol, methanol, and acetic acid, and the organic solvent of the mixed solvent may be at least one selected from the group consisting of ethyl acetate, acetonitrile, methylene chloride, chloroform, and dioxane. The aqueous solution may be distillated water, water for injection, or buffer solution.

In step (b'), the organic solvent is removed by evaporation.

In step (c'), the mixture remaining after evaporation of the organic solvent is dissolved in an aqueous solution, whereby the complex of the negatively charged drug and the cationic lipid is entrapped in the micelle structure of the amphiphilic block copolymer. The aqueous solution and the amount used thereof are as described above.

In yet another embodiment, the preparation method of the present invention may further comprise, after step (d) or (c'), step (e) of adding a freeze-drying additive to the micelle to freeze-dry the micelle.

In one embodiment, the preparation method of the present invention may further comprise, before freeze-drying step (e), a step of sterilizing the polymeric micelle aqueous solution, obtained in step (d) or (c'), with a sterilization filter.

In one embodiment, the freeze drying additive may be at least one selected from the group consisting of lactose, mannitol, sorbitol, and sucrose. The freeze drying additive is added to allow the freeze-dried composition to be maintained in a cake form. In another embodiment, the content of the freeze drying additive may be 1 to 90 wt %, preferably 10 to 60 wt %, based on the total dry weight of the freeze-dried composition.

In another embodiment of the present invention, the composition may be in the form of a micelle containing the negatively charged drug, the cationic lipid and a surfactant. Specifically, the present invention provides a micelle composition comprising a negatively charged drug, a cationic lipid of formula 1 and a surfactant, wherein the negatively charged drug forms a complex with the cationic lipid, and the complex is entrapped in the micelle structure of the surfactant.

The surfactant may be, for example, at least one selected from the group consisting of Tween-20, polyethylene glycol monooleyl ether, ethylene glycol monododecyl ether, diethylene glycol monohexyl ether, trimethylhexadecyl ammonium chloride, dodecyltrimethyl ammonium bromide, cyclohexylmethyl β-D-maltoside, pentaerythrityl palmitate, lauryldimethylamine-oxide, and N-lauroylsarcosine sodium salt.

In one embodiment of the present invention, the liposome formulation may comprise a complex of the negatively charged drug and the cationic lipid, and a cell-fusogenic phospholipid. Preferably, in order to increase the intracellular delivery efficiency of the negatively charged drug, the composition of the present invention may further comprise a cell-fusogenic phospholipid in an amount of 0.01 to 50 wt %, particularly 0.1 to 10 wt %, based on the total weight of the composition. The complex may be bound to the inside or surface of the liposome.

Specifically, the present invention provides a liposome composition comprising a negatively charged drug, a cationic lipid of formula 1 and a cell-fusogenic phospholipid, wherein the negatively charged drug forms a complex with the cationic lipid, and the complex is bound to a liposome consisting of the cell-fusogenic phospholipid.

Examples of the cell-fusogenic phospholipid may include dioleoylphosphatidylethanolamine (DOPE), 1,2-dipalmitoleoyl-sn-glycero-3-phosphocholine (DPPC), 1,2-dioleoyl-sn-glycero-3-phosphocholine (DOPC), 1,2-dipalmitoleoyl-sn-glycero-3-phosphoethanolamine (DPPE), etc. In order to increase the in vivo stability of the liposome, the cell-fusogenic phospholipid may be modified with at least one selected from the group consisting of polyalkyeneglycol, polyvinylalcohol, polyvinylpyrrolidone, polysaccharides, and derivatives thereof. Specifically, the cell-fusogenic phospholipid may be modified with at least one selected from the group consisting of monomethoxy polyethylene glycol, monoacetoxy polyethylene glycol, polyethylene glycol, a copolymer of polyethylene and propylene glycol, polyvinyl pyrrolidone, and dextran.

In another embodiment of the present invention, the above formulation may be in the form of an emulsion comprising a complex of the negatively charged drug and the cationic lipid and a surfactant. Specifically, the present invention provides an emulsion composition comprising a negatively charged drug, a cationic lipid of formula 1 and a surfactant, wherein the negatively charged drug forms a complex with the cationic lipid, and the complex is entrapped in an emulsion.

Examples of the surfactant that is contained in the emulsion formulation may include cationic, zwitterionic and nonionic surfactants. Examples of the cationic surfactant that may be used in the present invention include cetyl trimethylammonium bromide, hexadecyl trimethyl ammonium bromide, etc., and examples of the zwitterionic surfactant that may be used in the present invention include dodecyl betaine, dodecyl dimethylamine oxide, 3-(N,Ndimethylpalmitylammonio) propane sulfonate, etc. Also, examples of the nonionic surfactant that may be used in the present invention include Tween-20, Tween-80, Triton-X-100, polyethylene glycol monooleyl ether, triethylene glycol monododecyl ether, octyl glucoside, N-nonanoyl-Nmethylglucamine, etc.

The inventive drug delivery composition for delivering a negatively charged drug, which consists of a formulation such as a cationic liposome, a micelle or emulsion formulation, can significantly enhance the delivery efficiency of a desired negatively charged drug into animal cells and also reduces the cytotoxicity of the negatively charged drug.

In one embodiment, the pharmaceutical composition according to the present invention may be formulated in the form of an aqueous solution, a powder or a tablet. In another embodiment, the composition may be a formulation for injection. Also, the powder formulation may be reconstituted with distillated water for injection, 0.9% saline solution, 5% dextrose aqueous solution, and the like.

The pharmaceutical composition formed according to the preparation method of the present invention is stable in blood, and has a particle size of 10-200 nm, and preferably 10-150 nM.

The negatively charged drug-containing pharmaceutical composition of the present invention may be administered intravenously, intramuscularly, subcutaneously, orally, intraosseously, transdermally, locally, and the like, and the pharmaceutical composition may be formulated in various forms such as a solution, a suspension for injection, a tablet, a capsule, and the like.

Advantageous Effects

The cationic lipid according to the present invention forms a complex with a negatively charged drug such as a nucleic acid or an anionic active substance to allow the intracellular delivery of the negatively charged drug. Also, the cationic lipid together with additional components can form a liposome, micelle, emulsion or nanoparticle formulation to increase the blood or in vivo stability of the negatively charged drug. Moreover, the delivery systems reduce the cytotoxicity of the positive charge of the cationic lipid and also significantly the efficiency of intracellular delivery of nucleic acid. Thus, the cationic lipid will be useful as a drug delivery carrier capable of increasing the therapeutic effect of a nucleic acid or an anionic active substance.

Also, the cationic lipid of formula 1 can be easily synthesized in high yield using inexpensive oligoalkyleneamine with a fatty acid derivative and is purified in a very simple manner, unlike existing synthetic lipids.

Particularly, when the negatively charged drug of the composition of the present invention is a nucleic acid, it can be introduced into cells to treat various diseases, such as tumors, arthritis, or diseases of the cardiovascular system or the endocrine system, which are caused by the abnormal expression or over-expression of pathogenic proteins.

MODE FOR INVENTION

Hereinafter, the present invention will be described in further detail with reference to examples. It is to be understood, however, that these examples are for illustrative purposes only and are not intended to limit the scope of the present invention in any way.

Example 1

Synthesis of 1,6-dioleoyl triethylenetetramide 1,6-dioleoyl triethylenetetramide was synthesized in the following manner by a nucleophilic addition reaction between triethylenetetramine and oleoyl chloride.

1.12 g (7.5 mmol) of triethylenetetramine was added to 25 mL of dichloromethane and dissolved with stirring in an ice water bath at 5° C. for 30 minutes. To the solution, a solution of 2.00 g (6.0 mmol) of oleoyl chloride in 20 mL of dichloromethane in a separate reactor was added slowly dropwise while it was allowed to react at 5° C. for 3 hours. Due to hydrogen chloride produced during the reaction, unreacted triethylenetetramine HCl was precipitated. Before the end of the reaction, the upper layer solution was taken and analyzed by thin layer chromatography (TLC) with a mobile phase of ethanol:chloroform (2:1) to determine whether the reaction was completed. After it was determined that the reaction had completed, the precipitate was removed using filter paper.

Then, the filtered upper layer solution was evaporated in a rotary evaporator to remove the solvent and dried with a vacuum pump equipped with a cold trap. The resulting material was dissolved in 35 mL of diethyl ether and then extracted twice with 10 mL of 0.5 M NaOH in a separator funnel.

Figure 1:
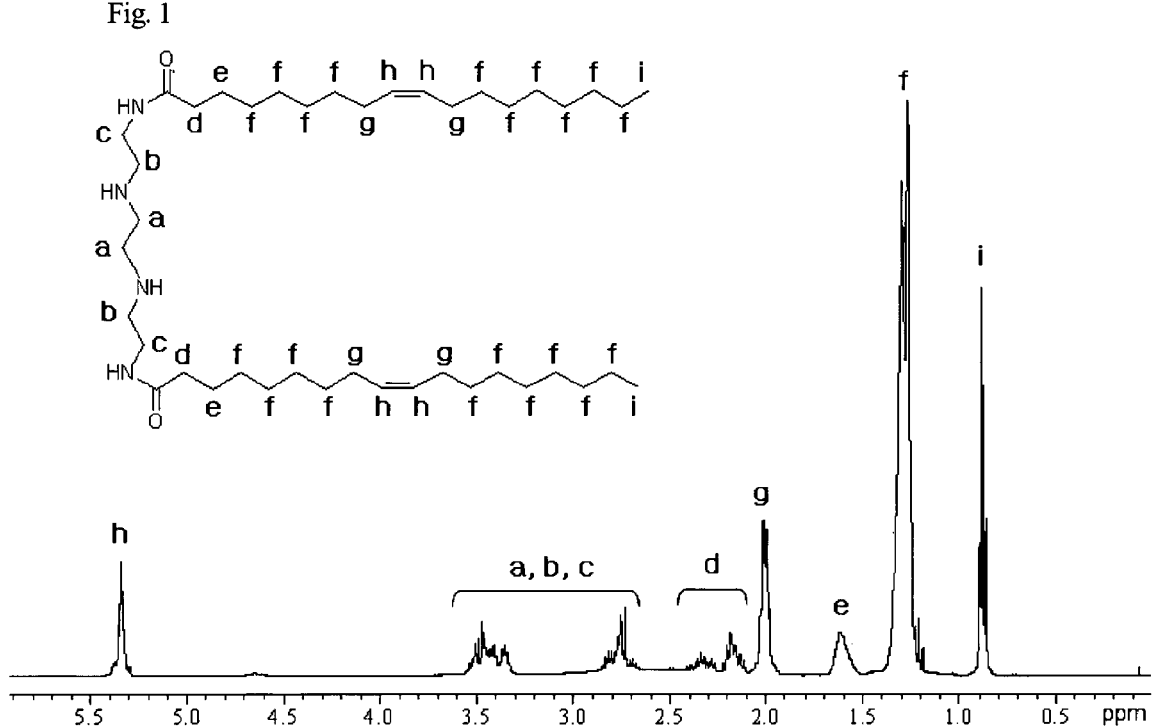
FIG. 1 shows the results of $^1$H NMR measurement of 1,6-dioleoyl triethylenetetramide synthesized in Example 1.

Then, the upper organic solvent layer was heated and distilled under reduced pressure in a rotary evaporator to completely remove the solvent, after which the residue was analyzed by thin layer chromatography to determine whether it was purified. The structure of the resulting product and the degree of introduction of an oleoyl group in the product were measured by a $^1$H NMR spectrometer, and the results of the measurement are shown in FIG. 1. The yield of the product was 89.1%, and 2.1 equivalents of the oleoyl group was introduced to triethylenetetramine.

Example 2

Figure 2:
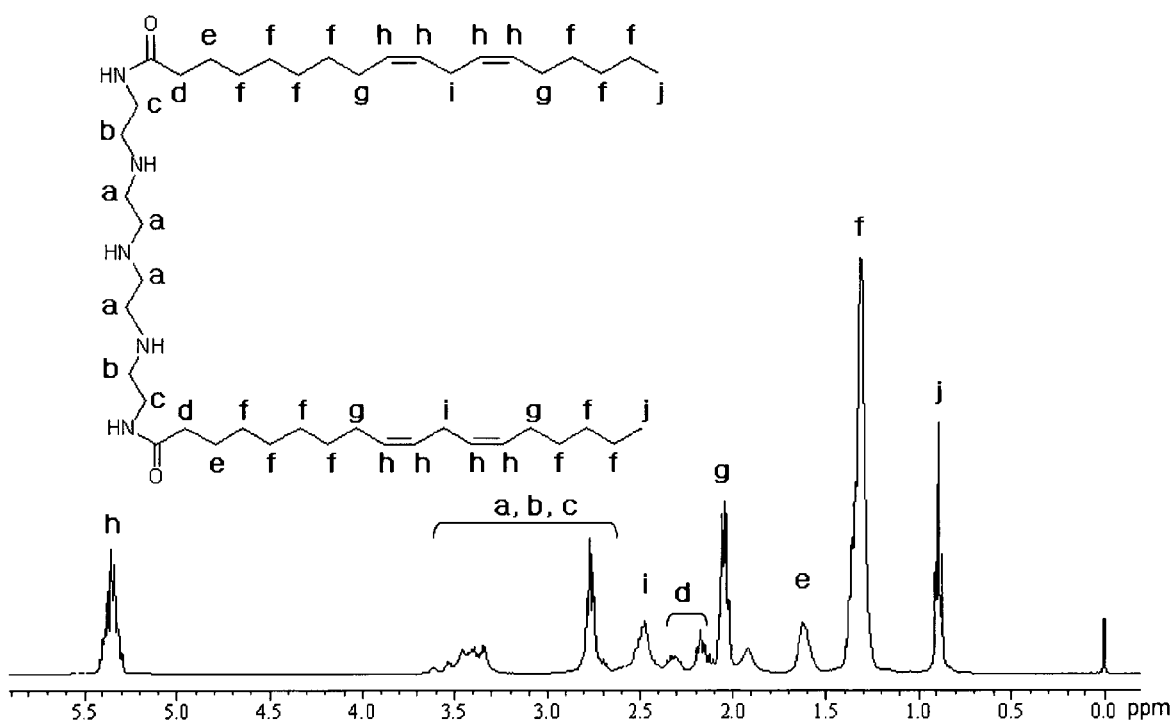
FIG. 2 shows the results of $^1$H NMR measurement of 1,8-dilinoleoyl tetraethylenepentamide synthesized in Example 2.

Synthesis of 1,8-dilinoleoyl tetraethylenepentamide 1,8-dilinoleoyl tetraethylenepentamide was synthesized and purified in the same manner as Example 1, except that 6.2 mmol of linoleoyl chloride and 4.1 mmol of tetraethylenepentamine were used in place of triethylenetetramine and oleoyl chloride. The structure of the resulting product and the degree of introduction of a linoleoyl group in the product were measured by a $^1$H NMR spectrometer, and the results of the measurement are shown in FIG. 2. The yield of the product was 78.9%, and 1.9 equivalents of the linoleoyl group was introduced to tetraethylenepentamine.

Example 3

Figure 3:
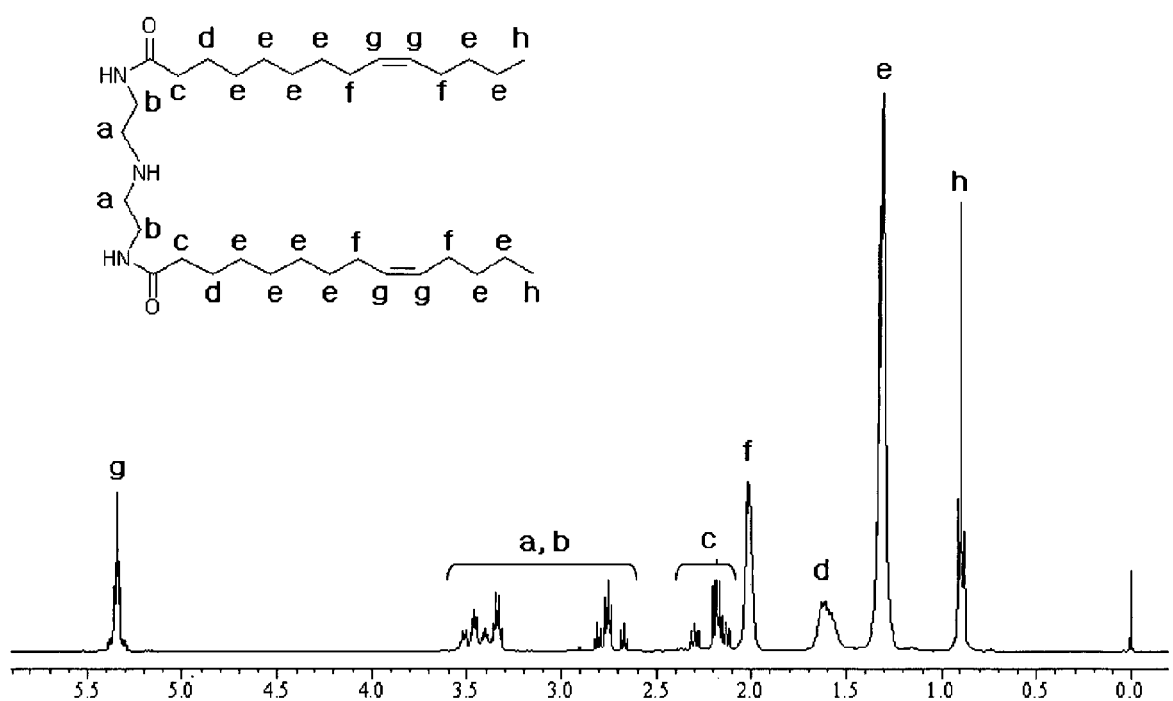
FIG. 3 shows the results of $^1$H NMR measurement of 1,4-dimyristoleoyl diethylenetriamide synthesized in Example 3.

Synthesis of 1,4-dimyristoleoyl diethylenetriamide 1,4-dimyristoleoyl diethylenetriamide was synthesized and purified in the same manner as Example 1, except that 8.1 mmol of myristoleolinoleoyl chloride and 13.5 mmol of diethylenetriamide were used in place of triethylenetetramine and oleoyl chloride. The structure of the resulting product and the degree of introduction of a myristoleolinoleoyl in the product were measured by a $^1$H NMR spectrometer, and the results of the measurement are shown in FIG. 3. The yield of the product was 80.4%, and 2.1 equivalents of the myristoleolinoleoyl group was introduced to diethylenetriamide.

Example 4

Figure 4:
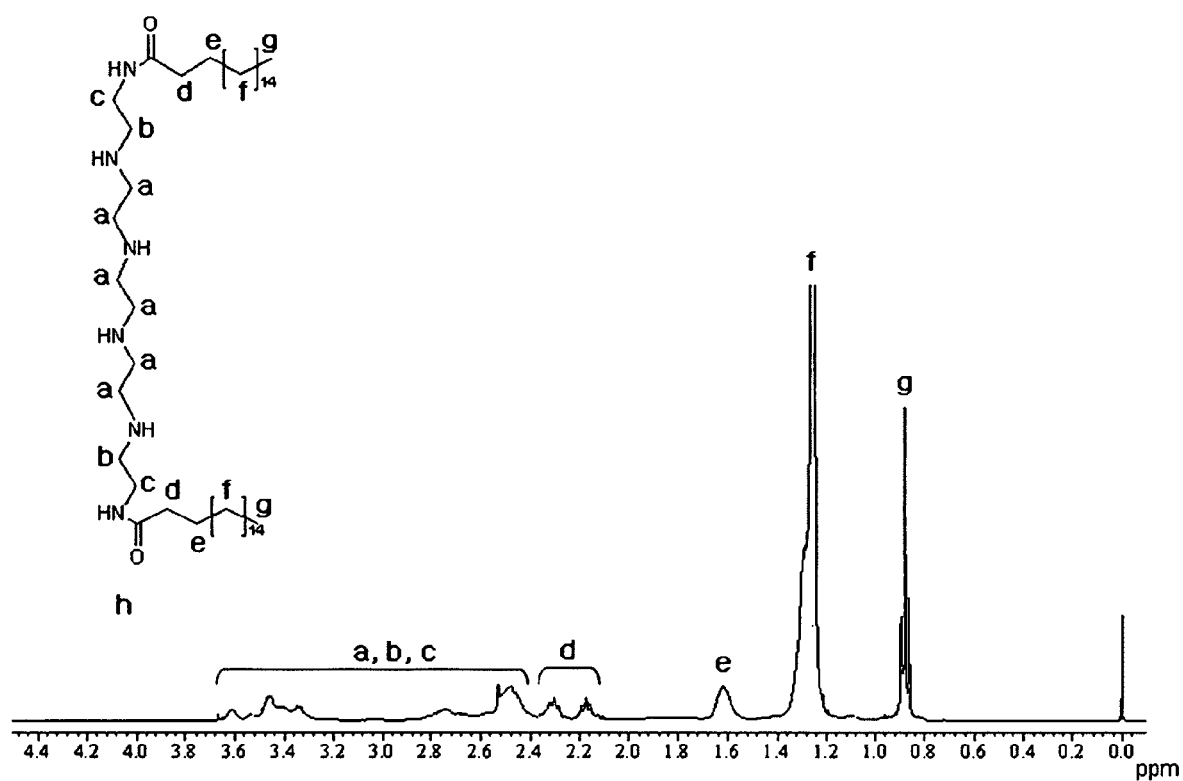
FIG. 4 shows the results of $^1$H NMR measurement of 1,10-disteroyl pentaethylenehexamide synthesized in Example 4.

Synthesis of 1,10-distearoyl pentaethylenehexamide 1,10-distearoyl pentaethylenehexamide was synthesized and purified in the same manner as Example 1, except that 4.2 mmol stearoyl chloride and 6.9 mmol of pentaethylenehexamine were used in place of oleoyl chloride and triethylenetetramine. The structure of the resulting product and the degree of introduction of a stearoyl in the product were measured by a $^1$H NMR spectrometer, and the results of the measurement are shown in FIG. 4. The yield of the product was 87.1%, and 2.0 equivalents of the stearoyl group was introduced to pentaethylenehexamine.

Example 5

Figure 5:
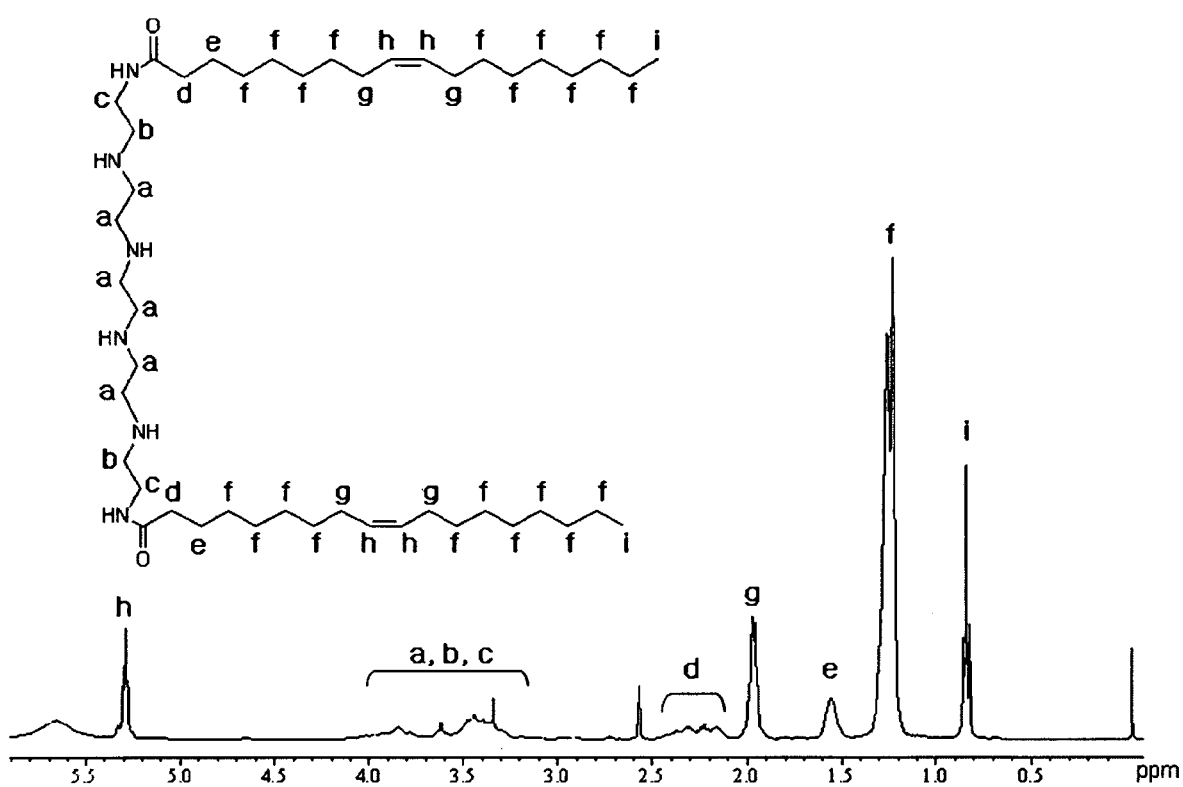
FIG. 5 shows the results of $^1$H NMR measurement of 1,10-dioleoyl pentaethylenehexamide synthesized in Example 5.

Synthesis of 1,10-dioleoyl pentaethylenehexamide 1,10-dioleoyl pentaethylenehexamide was synthesized and purified in the same manner as Example 1, except that 10.0 mmol of pentaethylenehexamine was used in place of triethylenetetramine. The structure of the resulting product and the degree of introduction of an oleoyl in the product were measured by a $^1$H NMR spectrometer, and the results of the measurement are shown in FIG. 5. The yield of the product was 88.2%, and 2.1 equivalents of the oleoyl group was introduced to pentaethylenehexamine.

Preparation Example 1

Synthesis of monomethoxy poly(ethylene glycol)-lactide (mPEG-PLA) block copolymer (A-B) (number-average molecular weights: 5,000-4,000 Da)

Figure 6:
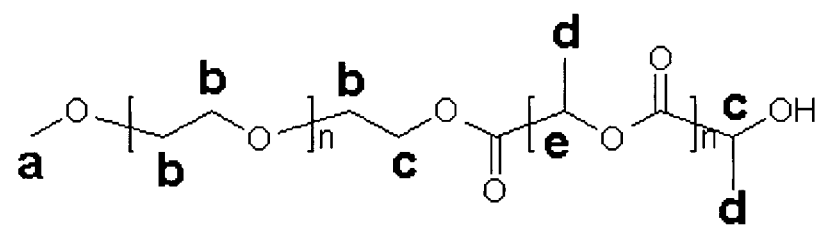
FIG. 6 shows the results of $^1$H NMR measurement of a mPEG-PLA block copolymer synthesized in Preparation Example 1.
Figure 6:
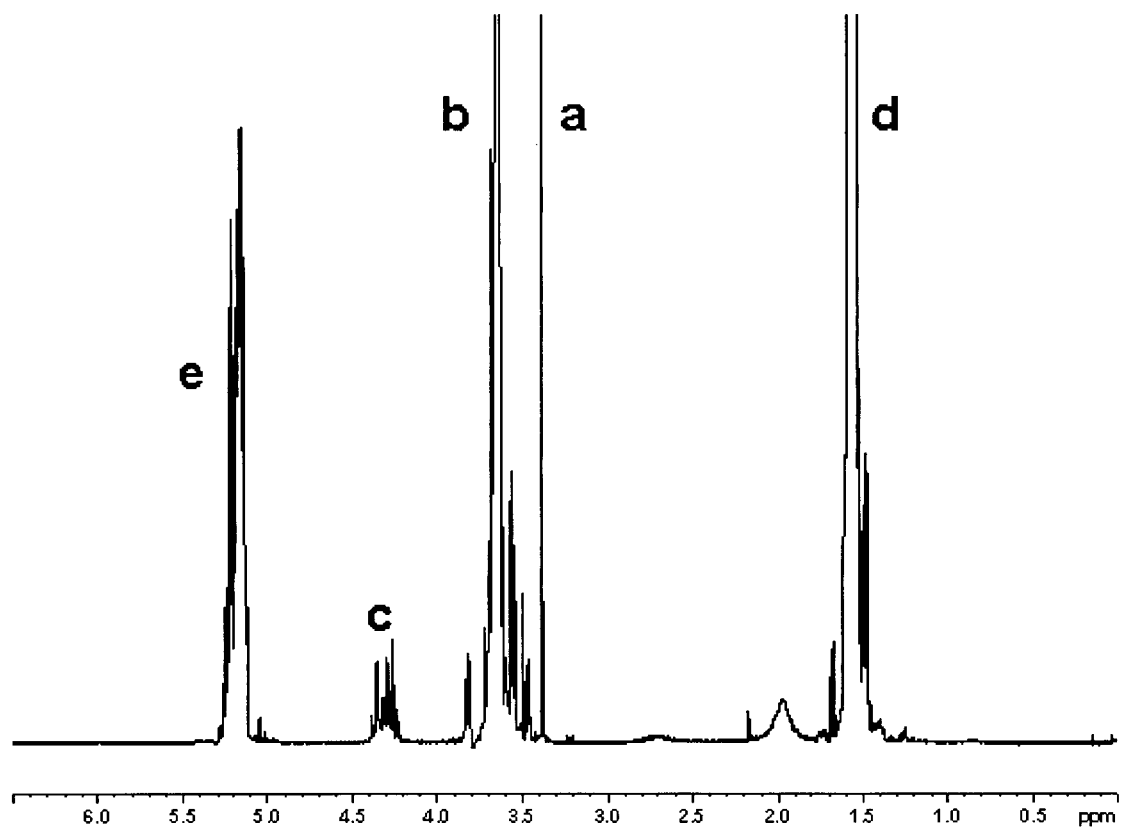

10 g of monomethoxy poly(ethylene glycol) (molecular weight: 5,000 Da) was placed in a 100-mL 2-neck round bottom flask and dried in a vacuum (1 mmHg) at 120° C. for 5 hours. The reaction flask was charged with dry nitrogen, and a 50% solution of a stannous octoate (Sn(Oct)$_2$) in toluene was injected into the flask together with 0.3 wt % (30 mg) of DL lactide with a syringe. The reaction mixture was stirred for 30 minutes and depressurized to 1 mmHg at 120° C. for 1 hour to remove toluene. 8.46 g of purified lactide was added thereto, and the mixture was heated at 130° C. for 6 hours. The mPEG-PLA obtained through the above process had number-average molecular weights of 5,000-4,000 Da and was determined to be an A-B type from the results of $^1$H-NMR in FIG. 6.

Preparation Example 2

Synthesis of mPEG-PLA-tocopherol (molecular weights: 5,000-4,000-530 Da)

Figure 7:
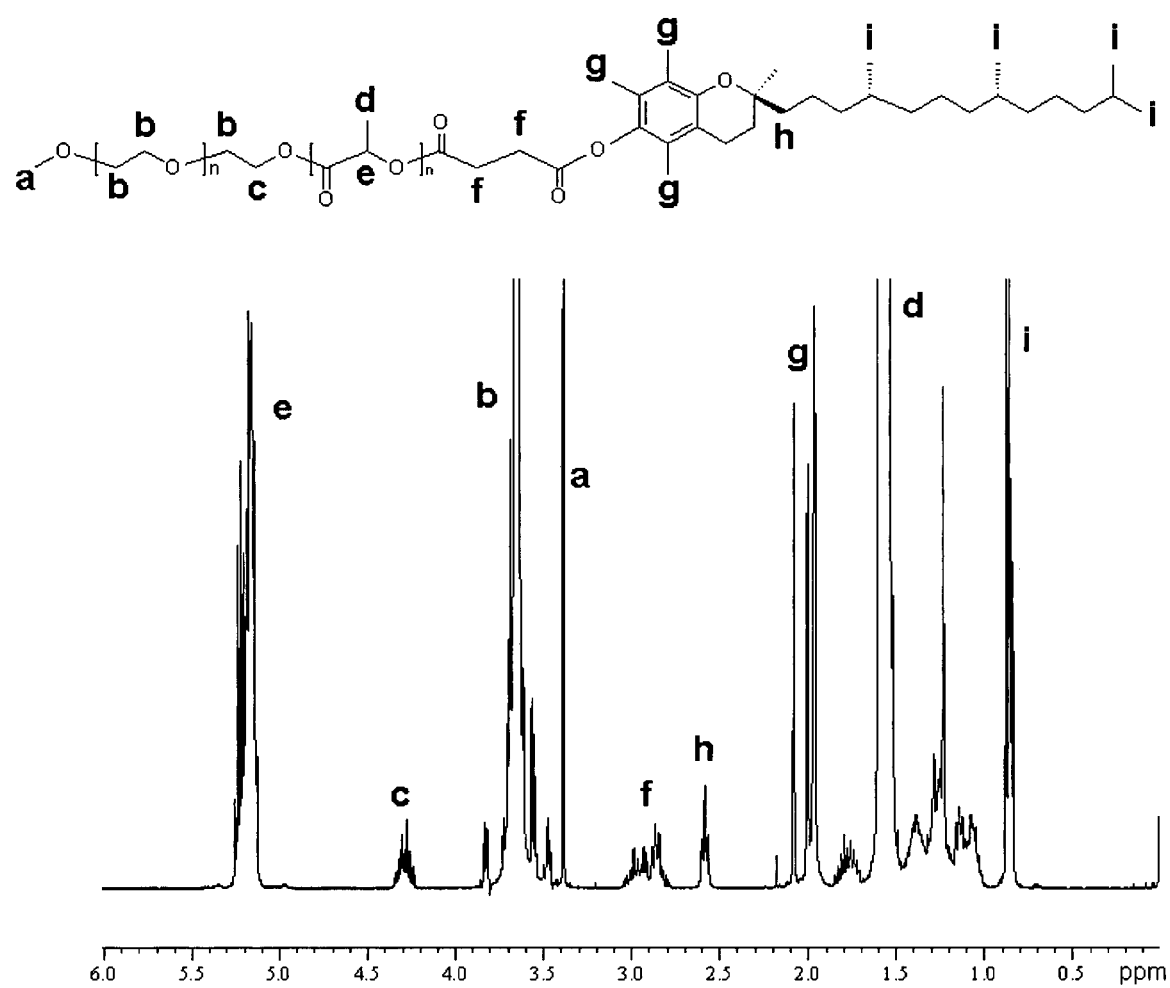
FIG. 7 shows the results of $^1$H NMR measurement of a mPEG-PLA tocopherol block copolymer synthesized in Preparation Example 2.

5 g of mPEG-PLA synthesized in Preparation Example 1 was placed in a 100-ml 2-neck round bottom flask and dried in a vacuum at 120° C. for 3 hours. A solution of 35.5 mg (645 μmol) of tocopherol succinyl chloride in 3 mL was added thereto and allowed to react at 100° C. for 8 hours in a vacuum. The resulting polymer was dissolved in dichloromethane and precipitated in heptane, whereby it was purified. The purified polymer was dried in a vacuum to give while powder particles. The yield of the product was 94.2%, and as can be seen from the results of $^1$H-NMR analysis in FIG. 7, the purity was 97.0% or more, and the rate of introduction of tocopherol was 99.9%.

Preparation Example 3

Synthesis of AC-cholesterol (3-beta[N-(aminoethane)carbamoyl]cholesterol)

In order to compare intracellular delivery efficiency with that of the cationic lipid of the present invention, a known AC-cholesterol cationic lipid was synthesized in the following manner.

1 g (2.23 mmol) of cholesteryl chloroformate was dissolved in 20 ml of chloroform. The cholesteryl chloroformate solution was added slowly to a solution of a 20-fold equivalent of ethylenediamine in 30 ml of chloroform at 4° C., and then allowed to react at room temperature for 3 hours. After completion of the reaction, the solvent was removed using a rotary evaporator, and the residue was dissolved again in a small amount of chloroform, and then extracted with a saturated NaCl solution and NaCO$_3$ to recover the chloroform layer.

Then, the solvent was removed using a rotary evaporator, and the residue was dissolved again in chloroform and separated by silica-gel chromatography. To the fraction eluted in the chloroform:methanol=9:1 (v/v), a hydrochloric acid solution was added in an amount of 50 equivalents relative to cholesteryl chloroformate, and methanol was added thereto in small amounts until a single phase was formed, thereby forming AC-cholesterol hydrochloride.

Figure 8:
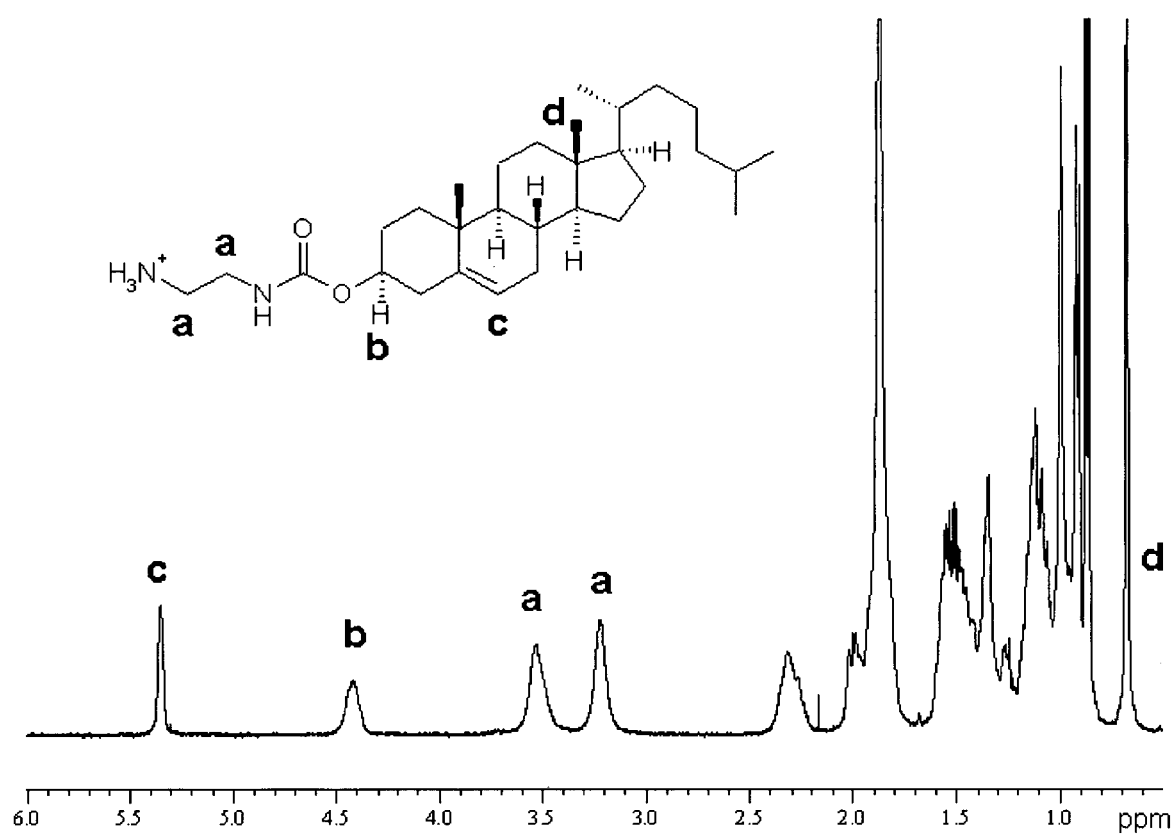
FIG. 8 shows the results of $^1$H NMR measurement of an AC-cholesterol synthesized in Preparation Example 3.

Then, the solvent was completely removed using a rotary evaporator, and the remaining AC-cholesterol HCl was dissolved in methanol at 60° C. and then cooled to 4° C., whereby it was recrystallized. The yield of the product was 51%. Whether AC-cholesterol was synthesized was analyzed by $^1$H NMR spectrometer, and the results of the analysis are shown in FIG. 8.

Example 6

Preparation of cationic liposome containing 1,6-dioleoyl triethylenetetramide 6-1: Preparation of Cationic Liposome Containing Cationic Lipid Each of 1.3 mg of the cationic lipid 1,6-dioleoyl triethylenetetramide synthesized in Example 1 and 1.7 mg of the cell-fusogenic phospholipid DOPE (Avanti polar lipids) was dissolved in 1 mL of chloroform, and then the two solutions were mixed in a 1-neck round bottom flask. Then, chloroform was slowly removed from the mixture in a rotary evaporator, thereby preparing a thin lipid film. 1 mL of phosphate buffered saline was added to the lipid film which was then stirred at 37° C. for 3 minutes, thereby preparing a liposome. The liposome solution was passed several times through an extruder equipped with a polycarbonate membrane having a pore size of 0.2 thereby preparing a liposome having a uniform particle size. The cationic liposome thus prepared was stored at 4° C. prior to use.

6-2: Incorporation of GFP siRNA 0.5 μl of the liposome solution prepared in Example 6-1 was added to and mixed with an Opti-MEM serum culture (Invitrogen). 2 μl (34 ng/μl) of GFP siRNA (comprising strands of SEQ ID NOs: 1 and 2) purchased from ST Pharm Co., Ltd. (Korea) was added to the liposome solution and mixed with a stirrer. The liposome formulation was stored at room temperature for 20 minutes, and then added to a cell line culture.

```
GFP siRNA (ST Pharm Co., Ltd., Korea)
Sense strand:
                              (SEQ ID NO: 1-dTdT)
5'-GCAAGCUGACCCUGAAGUUdTdT-3'

Antisense strand:
                              (SEQ ID NO: 2-dTdT)
5'-AACUUCAGGGUCAGCUUGCdTdT-3'
```

Example 7

Preparation of mPEG-PLA micelle containing 1,6-dioleoyl triethylenetetramide The ratio of the negative ion charge of siRNA to the positive ion charge of the cationic lipid, (N/P ratio), was set at 6, and an siRNA-cationic lipid complex having an N/P ratio of 6 was prepared in the same manner.

In a 1-neck round bottom flask, 33 μl of 1,6-dioleoyl triethylenetetramide prepared in Example 1 was mixed with 100 μl of chloroform and 100 μl of ethanol and completely dissolved at room temperature, and the solution was added to 100 μl of the solution containing 5 μg of siRNA, prepared in Example 6-2. 100 μl of distilled water and 100 μl of chloroform were added thereto to subject the solution to phase separation. After phase separation, only the chloroform layer was collected, thus obtaining a siRNA-cationic lipid complex.

9 mg of mPEG-PLA of Preparation Example 1 and 34 μg of DOPE were added to the complex and stirred at 60° C. for 5 minutes. Herein, the ratio of the siRNA/1,6-dioleoyl triethylenetetramide complex to mPEG-PLA was set at 0.42 wt %. The mixture was distilled under reduced pressure in a rotary evaporator to remove the solvent. 300 μl of distilled water was added to the flask which was then gently shaken, thereby preparing a polymeric micelle delivery system.

Example 8

Preparation of mPEG-PLA-tocopherol containing 1,6-dioleoyl triethylenetetramide A siRNA/1,6-dioleoyl triethylenetetramide/mPEG-PLA-tocopherol micelle delivery system was prepared in the same manner as Example 7, except that mPEG-PLA-tocopherol of Preparation Example 2 was used in place of mPEG-PLA. Herein, the ratio of the siRNA/1,6-dioleoyl triethylenetetramide complex to mPEG-PLA-tocopherol was set at 0.42 wt %. The mixture was distilled under reduced pressure in a rotary evaporator to remove the solvent. 300 μl of distilled water was added to the flask which was then gently shaken, thereby preparing a polymeric micelle delivery system.

Comparative Example 1

Preparation of mPEG-PLA-tocopherol containing AC-cholesterol

In order to compare intracellular delivery efficiency with that of the cationic lipid formulation of the present invention, a mPEG-PLA-tocopherol micelle was prepared in the same manner as Example 6 using 46 μg of AC-cholesterol (synthesized in Preparation Example 3), such that the ratio of the negative ion charge of 5 μg siRNA of Example 6-2 to the positive charge of the complex, (N/P ratio), was 6. Herein, the ratio of the siRNA/AC-cholesterol complex to mPEG-PLA-tocopherol was set at 0.57 wt %.

Example 7

Preparation of cationic emulsion containing 1,6-dioleoyl triethylenetetramide To 5.5 mg of the cationic lipid 1,6-dioleoyl triethylenetetramide prepared in Example 1, a 0.1-fold molar ratio of 1.0 mg of Tween-80 was added. 10 mL of phosphate buffered saline was added thereto, and the mixture was homogenized using a homogenizer at room temperature for about 2 minutes, thereby preparing an oil-in-water (O/W) cationic emulsion. 2.5 μl of the cationic emulsion was added to and mixed with 15.5 μl of an Opti-MEM serum culture (Invitrogen). 2 μl (34 ng/μl) of GFP siRNA of Example 6-2 was added thereto and the mixture was stirred, thus obtaining an emulsion. The emulsion formulation was stored at room temperature for 20 minutes, and then added to a cell line culture.

Test Example 1

Evaluation of siRNA Delivery Efficiency of Cationic Lipid-Containing Delivery Formulation by Analysis of Protein Expression The A549 GFP cell line that stably expresses green fluorescence protein (GFP) was treated with each of the formulations prepared in Examples 6 to 9 and Comparative Example 1, and the expression of GFP protein in the cells was examined.

Specifically, $1 \times 10^4$ cells were dispensed into each well of a 96-well cell culture plate, and after 24 hours, the cells in each well were determined to be grown to a confluency of about 60-70%. Then, the medium in each well was removed and 80 μl of 10% serum-containing fresh medium was added to each well. Then, 20 μl of each of the compositions of Examples 6 to 9 and Comparative Example 1, which contain 15 nM siRNA, was added to each well, and the cells were cultured in a 5% $CO_2$ incubator at 37° C. for 24 hours, followed by replacement with fresh medium. Meanwhile, a control group was treated with phosphate buffered saline (PBS) alone.

After 24 hours, the medium in each well was removed, after which each well was washed three times with PBS. In order to evaluate the inhibition of expression of GFP protein caused by each of the GFP siRNA delivery systems, the fluorescence of GFP in the cells was measured with a microplate reader (BioTek, Synergy HT Multi-mode microplate reader) (excitation wavelength: 485/20 nm, and emission wavelength: 528/20 nm). Also, the control group treated with PBS alone was evaluated. After the GFP fluorescence was measured, the cells were subjected to the SRB viability assay using the sulforhodamine B reagent, and then the UV absorbance at 540 nm was measured, thereby determining cell viability. Correction was performed by dividing the GFP fluorescence by the cell viability, and the results of the correction are shown in Table 1 below. Also, comparison with the commercially available delivery system lipofectamine (LipofectAMINE 2000, Invitrogen, USA) was performed.

TABLE 1

| Composition | GFP fluorescence (%) | Cell viability (%) | GFP fluorescence/cell viability (%) |
|---|---|---|---|
| Control | 99.1 | 99.9 | 99.2 |
| Lipofectamine | 46.9 | 72.1 | 65.0 |
| Comparative Example 1 | 65.4 | 90.2 | 72.5 |
| Example 6 | 51.0 | 89.5 | 57.0 |
| Example 7 | 51.5 | 91.5 | 56.3 |
| Example 8 | 51.3 | 97.0 | 52.9 |
| Example 9 | 55.4 | 98.1 | 56.5 |

As can be seen in Table 1 above, the compositions prepared in the Examples of the present invention efficiently delivered siRNA into cells even at very low siRNA concentrations and inhibited the expression of the target protein GFP by about 35 to 50%. Also, these compositions inhibited the expression of GFP protein to levels similar to or higher than that achieved by Lipofectamine while they showed higher cell viability. This suggests that the compositions of the present invention were less cytotoxic than Lipofectamine while exhibiting excellent activity. In addition, it can be seen that the siRNA delivery efficiency of the compositions of the present invention was about 30% higher than that of Comparative Example 1.

Test Example 2

Evaluation of siRNA Delivery Efficiency of Cationic Lipid-Containing Delivery Formulation by Analysis of mRNA Expression For the compositions of Examples 6 to 9 and Comparative Example 1, the efficiency of siRNA delivery into cells was evaluated at the mRNA level. The treatment conditions that were used on each of the delivery formulations were the same as those used in Test Example 1, but siRNA was used at varying concentrations of 5 nM and 15 nM, and the expression of GFP mRNA in cells was measured in the following manner using qRT-PCR (quantitative Reverse Transcription-Polymerase Chain Reaction).

Specifically, cells were treated by each of the delivery formulations in a 96-well plate, and after 48 hours, the cell culture medium in each well was removed, and then each well washed three times with PBS. Total RNA was isolated from the cells using Trizol reagent (Invitrogen), and the isolated RNA was reverse-transcribed (RT) to cDNA using a high-capacity RNA-to-cDNA MasterMix (Invitrogen). The reverse-transcribed cDNA was amplified by PCR. In this manner, glyceraldehyde-3-phosphate dehydrogenase (GAPDH) mRNA was amplified from the above-isolated RNA, and the expression of GFP mRNA was quantified. Meanwhile, a control group was treated with PBS alone. The results of the quantification are shown in Table 2 below.

TABLE 2

| Composition | siRNA concentration (nM) | GFP mRNA expression (%) |
|---|---|---|
| Control | 0 | 100.0 |
| Lipofectamine | 5 | 60.2 |
|  | 15 | 14.1 |
| Comparative Example 1 | 5 | 88.3 |
|  | 15 | 38.9 |
| Example 6 | 5 | 56.7 |
|  | 15 | 6.2 |
| Example 7 | 5 | 61.2 |
|  | 15 | 9.5 |
| Example 8 | 5 | 49.1 |
|  | 15 | 3.6 |
| Example 9 | 5 | 55.2 |
|  | 15 | 6.3 |

As can be seen in Table 2 above, the compositions prepared in the Examples of the present invention showed a decrease in the expression of GFP mRNA in proportion to the concentration of siRNA. At a siRNA concentration as low as 5 nM, these compositions inhibited the expression of GFP mRNA by about 50%, and at a siRNA concentration of 15 nM, these compositions inhibited the expression of GFP mRNA by 95% or more. From the results in Table 2, it can be seen that the ability of the inventive compositions to inhibit gene expression was similar to that of Lipofectamine, and particularly, was about 2 times higher than that of Lipofectamine at a low siRNA concentration of about 5 nM. This suggests that the compositions of the Examples more efficiently inhibit the expression of the target mRNA than Lipofectamine. Also, in comparison with the results of Comparative Example 1, the siRNA delivery efficiency of the inventive compositions was increased by about 10 times or more at a low siRNA concentration of 5 nM as a result of using the cationic lipid of the present invention. Accordingly, it can be seen that the cationic lipid of the present invention can achieve higher siRNA delivery efficiency than that of existing cationic lipids, even when a smaller amount of siRNA is used.

The invention claimed is:

1. A pharmaceutical composition comprising a negatively charged drug and a cationic lipid selected from a group consisting of 1,6-dioleoyl triethylenetetramide, 1,8-dilinoleoyl tetraethylenepentamide, 1,4-dimyristoleoyl diethylenetriamide, 1,10-distearoyl pentaethylenehexamide, and 1,10-dioleoyl pentaethylenehexamide.

2. The pharmaceutical composition of claim 1, wherein the composition is in the form of a liposome, a micelle, an emulsion or a nanoparticle.

3. The pharmaceutical composition of claim 1, wherein the ratio of the charge of the anionic drug to the charge of the cationic lipid is 0.1 to 128.

4. The pharmaceutical composition of claim 1, wherein the cationic lipid is contained in an amount of 0.001 to 10 wt % based on the total weight of the composition.

5. The pharmaceutical composition of claim 1, wherein the composition is in the form of a micelle comprising a negatively charged drug, a cationic lipid, and an amphiphilic block copolymer, wherein the negatively charged drug forms a complex with the cationic lipid, and the complex is entrapped in the micelle structure of the amphiphilic block copolymer.

6. The pharmaceutical composition of claim 1, wherein the composition is in the form of a liposome comprising a negatively charged drug, a cationic lipid, and a cell-fusogenic phospholipid, wherein the negatively charged drug forms a complex with the cationic lipid, and the complex is bound to a liposome formed from the cell-fusogenic phospholipid.

7. The pharmaceutical composition of claim 1, wherein the composition is in the form of a micelle comprising a negatively charged drug, a cationic lipid, and a surfactant, wherein the negatively charged drug forms a complex with the cationic lipid, and the complex is entrapped in the micelle structure of the surfactant.

8. The pharmaceutical composition of claim 1, wherein the composition is in the form of an emulsion comprising a negatively charged drug, a cationic lipid selected from a group consisting of 1,6-dioleoyl triethylenetetramide, 1,8-dilinoleoyl tetraethylenepentamide, 1,4-dimyristoleoyl diethylenetriamide, 1,10-distearoyl pentaethylenehexamide, and 1,10-dioleoyl pentaethylenehexamide, and a surfactant, wherein the negatively charged drug forms a complex with the cationic lipid, and the complex is entrapped in the emulsion.

9. The pharmaceutical composition of claim 1, wherein the negatively charged drug is an antisense oligonucleotide, an aptamer or a small interfering RNA (siRNA).

* * * * *